United States Patent
Gu et al.

(10) Patent No.: US 10,881,675 B2
(45) Date of Patent: Jan. 5, 2021

(54) GUT HEALTH COMPOSITIONS

(71) Applicants: Jennifer L. Gu, Diamond Bar, CA (US); Edward S. Lee, Diamond Bar, CA (US)

(72) Inventors: Jennifer L. Gu, Diamond Bar, CA (US); Edward S. Lee, Diamond Bar, CA (US)

( * ) Notice: Subject to any disclaimer, the term of this patent is extended or adjusted under 35 U.S.C. 154(b) by 201 days.

(21) Appl. No.: 16/158,257

(22) Filed: Oct. 11, 2018

(65) Prior Publication Data
US 2019/0105338 A1    Apr. 11, 2019

Related U.S. Application Data

(60) Provisional application No. 62/570,876, filed on Oct. 11, 2017.

(51) Int. Cl.
| | | |
|---|---|---|
| A61K 36/00 | (2006.01) | |
| A61K 31/702 | (2006.01) | |
| A61K 36/185 | (2006.01) | |
| A61P 1/14 | (2006.01) | |
| A61K 38/48 | (2006.01) | |
| A61K 9/20 | (2006.01) | |
| A61K 9/14 | (2006.01) | |
| A61K 9/28 | (2006.01) | |

(52) U.S. Cl.
CPC .......... *A61K 31/702* (2013.01); *A61K 9/2018* (2013.01); *A61K 9/2027* (2013.01); *A61K 9/2059* (2013.01); *A61K 36/185* (2013.01); *A61K 38/4873* (2013.01); *A61P 1/14* (2018.01); *A61K 9/14* (2013.01); *A61K 9/2813* (2013.01); *A61K 9/2826* (2013.01)

(58) Field of Classification Search
None
See application file for complete search history.

(56) References Cited

U.S. PATENT DOCUMENTS

| | | |
|---|---|---|
| 2009/0074678 A1 | 3/2009 | Yoshimatsu |
| 2010/0143319 A1 | 6/2010 | Weir |

FOREIGN PATENT DOCUMENTS

WO    2016085356 A1    6/2016

OTHER PUBLICATIONS

International Search Report and Written Opinion for corresponding PCT Application No. PCT/US2018/055517, 8 pages, dated Jan. 2, 2019.
Nieto-Dominguez et al. "Preblotic effect of xylooligosaccharides produced from birchwood xylan by a novel fungal GH11 xylanase" Food Chemistry, 2017; 232(1):105-113, Available online Mar. 29, 2017 (Mar. 29, 2017) (doi: 10.1 0161j.foodchem.2017.03.149).
Ansell et al. "Kiwifruit-derived supplements increase stool frequency in healthy adults: a randomized, double-blind, placebo-controlled study" Nutrition Research, 2015; 35(5):401-408 (doi: 10.1016/j.nutres.2015.04.005).
Yang et al. "Xylooligosaccharide supplementation alters gut bacteria in both healthy and prediabetic adults: a pilot study" Front Physiol. 2015; 6:216 (doi: 10.3389/fphys.2015.00216).

*Primary Examiner* — Qiuwen Mi
(74) *Attorney, Agent, or Firm* — Michelle L. Gross, P.C.

(57) ABSTRACT

Gut health compositions include xylooligosaccharides (XOS) and a kiwifruit extract powder, which may include one or both of a) green kiwifruit extract powder having >7,500, and preferably >25,000, AUs/g actinidin, and optionally about 4.8 mg GAE total phenolics/600 mg and b) gold kiwifruit extract powder having >5,000 AUs/g actinidin and optionally about 6.6 mg GAE total phenolics/600 mg. Xylobiose, xylotriose and/or xylotetraose account for 50-98% by weight of the XOS.

22 Claims, 1 Drawing Sheet

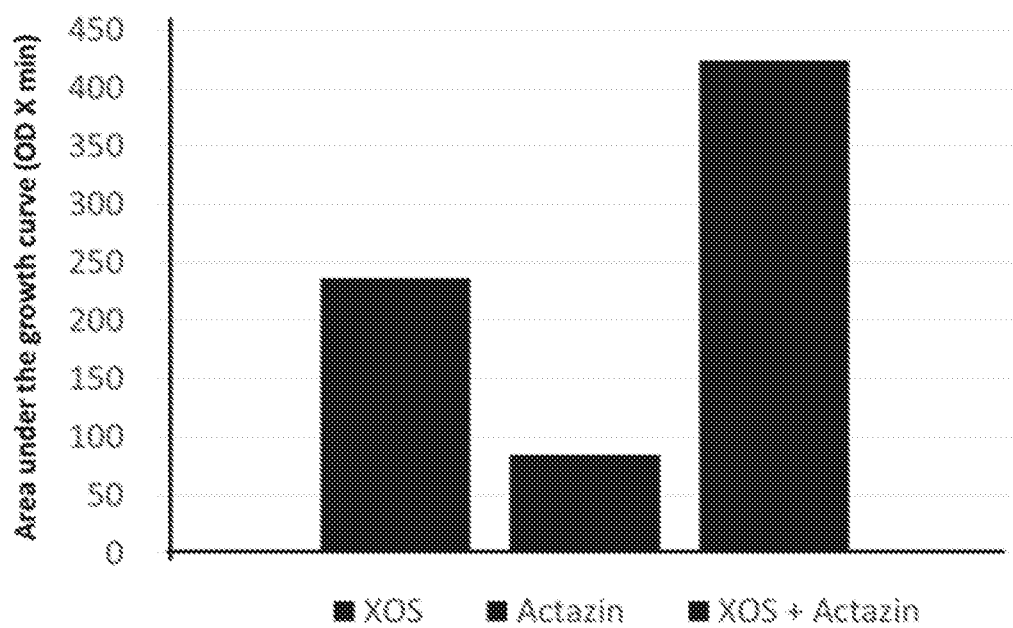

GUT HEALTH COMPOSITIONS

CROSS-REFERENCE TO RELATED APPLICATIONS

This application claims the benefit of U.S. Provisional Patent Application No. 62/570,876 filed Oct. 11, 2017, the entirety of which is incorporated herein by reference.

FIELD OF THE INVENTION

The disclosed subject matter relates to compositions for gut health for promoting and maintaining gut health.

BACKGROUND

The gastrointestinal tract is inhabited by different bacterial populations. The microorganisms populating the gut are primarily bacteria from more than 1,000 species, with 90 percent of these being firmicutes and bacteroidetes. Tremaroli V., Backhed F., Functional interactions between the gut microbiota and host metabolism. Nature 2012: 242-249; Robles A V, Guarner F., Linking the gut microbiota to human health. British Journal of Nutrition 2013. 109:S21-S26.

SUMMARY OF THE INVENTION

It is generally accepted there is a delicate balance between "friendly" and "unfriendly" microorganisms that is integral to good health and the prevention of disease. An imbalance or alteration of these populations can lead to a variety of health issues, including poor immune response, allergies, digestive disorders, high cholesterol and cardiovascular abnormality poor bone health, and metabolic imbalances.

Studies demonstrate that people who suffer from particular diseases have a different microbiota signature than healthy subjects. Healthy digestive function is closely associated with the microbiotic signature in the gut of an individual, therefore maintaining healthy gut microflora is pivotal to the health of individuals.

Probiotics, live bacteria found naturally in the digestive system, are considered "good" bacteria that can keep the digestive system healthy by controlling growth of harmful bacteria. There are many types of bacteria classified as probiotics, each having different benefits. The most well studied probiotics are *Bifidobacterium* and *Lactobacillus*. One of the best-known probiotic food sources is yogurt. Other probiotic food sources include sauerkraut, miso soup, fermented soft cheeses, and sourdough bread. The common feature of all these foods is fermentation, a process that produces probiotics.

Prebiotics are food ingredients that help support growth of probiotic bacteria. In effect, they are nutrients that serve as a "fertilizer" for the beneficial bacteria that already exist in the gut. Prebiotics are defined as selectively fermented ingredients that allow specific changes, both in the composition and/or activity in the gastrointestinal microflora. (Roberfroid M B. Prebiotics: The Concept Revisited. J Nutr. March 2007; 137 (3 Suppl 2): 830S-7S) The 2007 FAO Technical Meeting Report on Prebiotics defined them as a food component that confers a health benefit on the host associated with modulation of the microbiota. Food and Agriculture Organization of the United Nations (FAO). Technical Meeting Report on Prebiotics. Sep. 15-16, 2007.

Probiotics have been one of the fastest growing market trends in the supplement and functional food industries. Although probiotics have been shown to be effective in managing certain gastrointestinal conditions, they have specific limitations. Probiotics need to be delivered to the intestinal tract alive to be effective. However, they are extremely delicate-sensitive to heat and stomach acid, which can destroy them long before they reach the large intestine to colonize. Recent studies also indicate that most probiotic strains do not colonize the gut, but elicit their benefits while passing through the gut, thus limiting their benefits.

Prebiotics can modify microbiota by targeting bacteria that is already present in the large intestine. The majority of prebiotic products on the market are FOS- and GOS-based ingredients. However, xylooligosaccharides (XOS), naturally present in fruits, vegetables, bamboo, honey, and milk, can also change microbiota as an effective prebiotic. Studies have shown that XOS can change the microbiome in a selected fashion, thus improving microbiota to a metabolically balanced composition. Some prebiotic oligosaccharides may cause gas in the colon as they ferment. Larger amounts of gas can cause pain and cramping in the stomach.

An example of an XOS is PreticX™, a non-digestible XOS available from AIDP, Inc., Industry City, Calif., which is formed by connecting xylose molecules with a $\beta$1-4 glycosidic bond. PreticX™ is a prebiotic that boosts levels of beneficial bacteria in the human gut and acts as an effective soluble dietary fiber. PreticX™ is available in 70% and 95% forms as well as other forms with a lower percentage of XOS by weight of the composition. The 70% form contains >68% by weight XOS and the 95% form contains >93% by weight XOS. For example, 1400 mg of 70% PreticX™ contains greater than about 950 mg of XOS. Strong clinical data links PreticX™ with improved healthy microflora, especially increased bifidobacteria. In one study, tolerance and efficacy of XOS were evaluated in thirty-two healthy adult subjects, who were recruited in a double-blind, randomized, placebo-controlled study. Xylooligosaccharide increases bifidobacteria but not lactobacilli in human gut microbiota. (S. M. Finegold, Z. Li, P. H. Summanen, J. Downes, G. Thames, K. Corbett, S. Dowd, M. Krak, D. Heber. Food Funct. 2014 March; 5(3):436-45.) Subjects received 1 g PreticX™ XOS, 2 g PreticX™ XOS or placebo in daily doses. The study consisted of a two-week run-in, an eight-week intervention, and a two-week washout phase. Stool samples were collected at baseline, after four and eight weeks of intervention as well as two weeks after cessation of the intervention. The study showed that *bifidobacterium* counts increased in both PreticX™ XOS groups compared to the placebo subjects. The *bifidobacterium* count increased 21 percent from the baseline at four weeks and 17 percent from the baseline at eight weeks in the high dose (2 g per day) group.

Also significant, when the prebiotics were compared, researchers found that *bifidobacterium* favored PreticX™ XOS and confirmed findings from other human and animal studies, suggesting that XOS is an effective prebiotic that can change microbiota levels with a lower dose of 1 g per day (as PreticX™ XOS) as opposed to FOS and GOS, which requires daily doses between 8 g and 10 g. At these lower dose levels, the researchers also concluded that intestinal side effects were significantly reduced with XOS, as compared to other prebiotics.

Similar results were also observed in an earlier study published in the Korean Journal of Nutrition in 2007, where 14 Korean women were randomly assigned to two groups: 1.4 g/day of XOS and 2.8 g/day of XOS for 28 days. The number of fecal bifidobacteria were significantly increased after 28 days in the 1.4 g/day intake group (p<0.05), and in the 2.8 g/day intake group, the number of fecal bifidobacteria significantly increased after 14 days (p<0.05). Because XOS requires only a small efficacious dosage, it does not cause pain or cramping commonly associated with other prebiotics.

XOS not only demonstrates compelling efficacy in promoting healthy microbiota at low doses, it has also been shown to improve biomarkers associated with heart disease, diabetes and obesity. For example, in the 2007 study, there were significant increased fecal bifidobacterial counts, and the fecal triglyceride and cholesterol concentrations were increased in the high dose 2.8 g/day intake group (p<0.05). Serum triglyceride, cholesterol and glucose concentration were also significantly increased in the higher dose intake group (p<0.05). In the 1.4 g/day intake group, fecal cholesterol concentration also increased (p<0.05).

Green kiwifruits are excellent sources of vitamins A, C, and E, potassium, dietary fiber, and polyphenols. Drummond, L. (2013), The Composition and Nutritional Value of Kiwifruit. In Advances in Food and Nutrition Research (Vol. 68, pp. 33-57). Elsevier. https://doi.org/10.1016/B978-0-12-394294-4.00003-1. Whole kiwifruit consumption has been shown to have beneficial effects on constipation, with several clinical studies demonstrating its efficacy (Stonehouse, W., Gammon, C. S., Beck, K. L., Conlon, C. A., von Hurst, P. R., & Kruger, R. (2013). Kiwifruit: our daily prescription for health 1. Canadian Journal of Physiology and Pharmacology, 91(6), 442-447. https://doi.org/10.1139/cjpp-2012-0303) by improving laxation in healthy individuals (Chan, A. O. O. Increasing dietary fiber intake in terms of kiwifruit improves constipation in Chinese patients. World Journal of Gastroenterology, 13(35), 4771(2007). https://doi.org/10.3748/wjg.v13.i35.4771; Rush, et al. Kiwifruit promotes laxation in the elderly. Asia Pacific Journal of Clinical Nutrition, 11(2), 164-168(2002). https://doi.org/10.1046/j.1440-6047.2002.00287.x) and in patients with irritable bowel syndrome with constipation (Chang, C.-C., Lin, Y.-T., Lu, Y.-T., Liu, Y.-S., & Liu, J.-F. Asia Pac J Clin Nutr. 2010; 19(4):451-7. It is believed that the unique combination of soluble and insoluble fibers, polyphenols, and the enzyme actinidin that are present in kiwifruit confer these and other health benefits. Recently, a unique kiwifruit-derived supplement has been shown to increase stool frequency in healthy adults in a randomized, double-blind, placebo-controlled study. (Ansell, J., et al. Nutrition Research, 35(5), 401-408 (2015). https://doi.org/10.1016/j.nutres.2015.04.005).

Actazin™ and Livaux™ are powdered ingredients manufactured by Anagenix of Wellington, New Zealand and available from AIDP, Inc. derived from whole New Zealand green (*Actinidia deliciosa* "Hayward") and gold (*Actinidia chinensis* "Zesy200") kiwifruit, respectively, from which the skin and seeds are removed and the remaining flesh cold processed for use in food and dietary supplements. It is believed that kiwifruit components present in Actazin™ and Livaux™ improve stool frequency, stool form, and gastrointestinal comfort in healthy and constipated individuals.

A recent randomized, double-blind, placebo-controlled crossover study examining the effects of Actazin™ green kiwifruit extract (Actazin-L=low dose 600 mg, Actazin-H=high dose 2400 mg) and Livaux™ (gold kiwifruit extract, 2400 mg) on stool frequency, stool form and gastrointestinal comfort in healthy and functionally constipated individuals found that both investigational products were well-tolerated, and that supplementation with Actazin™-H and Livaux™ kiwifruit extracts demonstrated a significant and clinically meaningful increase in daily bowel movements by more than one bowel movement per week in healthy individuals. (Ansell, J., et al. Kiwifruit-derived supplements increase stool frequency in healthy adults: a randomized, double-blind, placebo-controlled study. Nutrition Research, 35(5), 401-408 (2015). https://doi.org/10.1016/j.nutres.2015.04.005, incorporated by reference herein in its entirety). No significant differences were observed in stool form as determined by use of the Bristol stool scale. In the functionally constipated cohort, there were no significant differences between interventions for bowel movements and the Bristol stool scale values.

Actazin™ and Livaux™ kiwifruit extracts are derived from natural sources, are safe, bioavailable, and address a longstanding unmet need for effective constipation intervention naturally. Disclosed herein are compositions including kiwifruit extracts such as but not limited to Actazin™ and/or Livaux™ in combination with an XOS prebiotic such as but not limited to PreticX™ in which xylobiose, xylotriose and/or xylotetraose account for 50-98% by weight of the total xylooligosaccharide profile of the XOS prebiotic. The compositions are safe and effective to increase stool frequency in otherwise healthy individuals having ≤3 complete spontaneous bowel movements per week. The compositions provide results that are surprisingly greater than what one skilled in the art would expect from the combination of an XOS and Actazin™ or Livaux™ kiwifruit extract powders.

As used herein with reference to disclosed embodiments, unless otherwise defined, the term XOS means and refers to XOS in which xylobiose, xylotriose and/or xylotetraose account for 50-98% by weight of the total xylooligosaccharide profile of the XOS.

In one embodiment a composition is disclosed including XOS and Actazin™ or Livaux™. In another embodiment a composition includes from 10 mg to 20 g of XOS and from 10 mg to 20 g of Actazin™ or Livaux™. In another embodiment a composition has from 10 mg to 20 g of XOS and from 10 mg to 20 g of a combination of Actazin™ and Livaux™. In another embodiment a composition has from 100 mg to 10 g of XOS and from 50 mg to 10 g of a combination of Actazin™ and Livaux™. In still another embodiment a composition has from 100 mg to 10 g of XOS and from 50 mg to 10 g of Actazin™ or Livaux™. In yet another embodiment a composition is disclosed having from 500 mg to 5 g of XOS and from 300 mg to 5 g of a combination of Actazin™ and Livaux™. In another embodiment a composition includes 500 mg to 5 g of XOS and 300 mg to 5 g of Actazin™ or Livaux™. In another embodiment a composition has from 1 g to 2 g of XOS and from 600 mg to 2.4 g of Actazin™ or Livaux™.

In another embodiment a composition has from 1 g to 2 g of XOS and from 600 mg to 2.4 g of a combination of Actazin™ and Livaux™. In one embodiment the composition includes 1-4 g of PreticX™ prebiotic (70%) and 600 mg of Actazin™ or Livaux™. In another embodiment the composition includes 500 mg-2 g of PreticX™ XOS prebiotic (95%) and 600 mg of Actazin™ or Livaux™. In one embodiment the composition includes 1-2 g of PreticX™ prebiotic (95%) and 600 mg of Actazin™ or Livaux™.

In one embodiment the composition includes 1-2 g of PreticX™ prebiotic (95%) and 600 mg of a combination of Actazin™ and Livaux™. In another embodiment the composition includes 500 mg-2 g of PreticX™ prebiotic (95%) and 600 mg of a combination of Actazin™ and Livaux™. In still another embodiment the composition includes PreticX™ having 1 g of XOS and 600 mg of a combination of Actazin™ and Livaux™. In yet another embodiment the composition includes PreticX™ having 1 g of XOS and 600 mg of Actazin™ or Livaux™.

As noted, xylobiose, xylotriose and/or xylotetraose account for 50-98% by weight of the total xylooligosaccharide profile of the XOS prebiotic, as measured by HPLC. This is the case for all PreticX™ XOS prebiotics regardless of the strength. In other embodiments xylobiose, xylotriose and/or xylotetraose account for 60-95% by weight of the total xylooligosaccharide profile of the XOS prebiotic. In still other embodiments xylobiose, xylotriose and/or xylotetraose account for at least 70% by weight of the total xylooligosaccharide profile of the XOS prebiotic. In yet other embodiments xylobiose, xylotriose and/or xylotetraose account for at least 80% by weight of the total xylooligosaccharide profile of the XOS prebiotic. In yet other embodiments xylobiose, xylotriose and/or xylotetraose account for at least 90% by weight of the total xylooligosaccharide profile of the XOS prebiotic.

Furthermore, in some embodiments xylobiose accounts for 25-70% by weight of the total xylooligosaccharide profile of the XOS prebiotic. In other embodiments xylobiose accounts for 30-60% by weight of the total xylooligosaccharide profile of the XOS prebiotic. In still other embodiments xylobiose accounts for at least 25% by weight of the total xylooligosaccharide profile of the XOS prebiotic. In still other embodiments xylobiose accounts for at least 30% by weight of the total xylooligosaccharide profile of the XOS prebiotic. In still other embodiments xylobiose accounts for at least 35% by weight of the total xylooligosaccharide profile of the XOS prebiotic. In still other embodiments xylobiose accounts for at least 40% by weight of the total xylooligosaccharide profile of the XOS prebiotic. In still other embodiments xylobiose accounts for at least 50% by weight of the total xylooligosaccharide profile of the XOS prebiotic.

In other embodiments xylotriose accounts for 20-50% by weight of the total xylooligosaccharide profile of the XOS prebiotic. In other embodiments xylotriose accounts for 25-35% by weight of the total xylooligosaccharide profile of the XOS prebiotic. In still other embodiments xylotriose accounts for at least 25% by weight of the total xylooligosaccharide profile of the XOS prebiotic. In still other embodiments xylotriose accounts for at least 30% by weight of the total xylooligosaccharide profile of the XOS prebiotic. In still other embodiments xylotriose accounts for at least 35% by weight of the total xylooligosaccharide profile of the XOS prebiotic.

In some embodiments xylotetraose may account for 5-25% by weight of the total xylooligosaccharide profile of the XOS prebiotic. In some embodiments xylotetraose accounts for 6-20% by weight of the total xylooligosaccharide profile of the XOS prebiotic. In other embodiments xylotetraose may account for at least 10% by weight of the total xylooligosaccharide profile of the XOS prebiotic. In other embodiments xylotetraose may account for at least 15% by weight of the total xylooligosaccharide profile of the XOS prebiotic. In other embodiments xylotetraose may account for at least 17% by weight of the total xylooligosaccharide profile of the XOS prebiotic.

In some embodiments disclosed herein, green kiwifruit extract powders have >7,500 AUs/g actinidin. In other embodiments green kiwifruit extract powders have >25,000 AUs/g actinidin. In still other embodiments, green kiwifruit extract powders contain about 4.8 mg GAE total phenolics/600 mg.

In some embodiments disclosed herein, gold kiwifruit extract powders have >5,000 AUs/g actinidin. In other embodiments gold kiwifruit extract powders contain about 6.6 mg GAE total phenolics/600 mg.

In still further embodiments, compositions may include XOS and a kiwifruit extract powder selected from the group consisting of a) green kiwifruit extract powder having >25,000 AUs/g actinidin and b) gold kiwifruit extract powder having >5,000 AUs/g actinidin. In some embodiments the composition includes 10 mg to 20 g of XOS and 10 mg to 10 g of one of the kiwifruit extract powders with the aforementioned properties. In some embodiments the composition includes 100 mg to 10 g of XOS and 50 mg to 10 g of one of the kiwifruit extract powders with the aforementioned properties, while in other embodiments the composition has 500 mg to 5 g of XOS and 300 mg to 5 g of one of the kiwifruit extract powders. In other cases the composition may include 500 mg to 2 g of XOS and 600 mg of one of the kiwifruit extract powders. In still further embodiments the composition may include 1 g to 2 g of XOS and 600 mg to 2.4 g of one of the kiwifruit extract powders. In one embodiment the composition includes 1 to 2 g of XOS and 600 mg of one of the kiwifruit extract powder.

In still further embodiments, compositions may include from 10 mg to 20 g of XOS and from 10 mg to 20 g of a kiwifruit extract powder selected from the group consisting of a) green kiwifruit extract powder containing about 4.8 mg GAE total phenolics/600 mg and >25,000 AUs/g actinidin and b) gold kiwifruit extract powder containing about 6.6 mg GAE total phenolics/600 mg and >5,000 AUs/g actinidin. In some embodiments the composition includes 100 mg to 10 g of XOS and 50 mg to 10 g of one of the kiwifruit extract powders with the aforementioned properties. In other embodiments the composition has 500 mg to 5 g of XOS and 300 mg to 5 g of one of the kiwifruit extract powders. In other cases the composition may include 500 mg to 2 g of XOS and 600 mg of one of the kiwifruit extract powders. In still further embodiments the composition may include 1 g to 2 g of XOS and 600 mg to 2.4 g of one of the kiwifruit extract powders. In one embodiment the composition includes 1 to 2 g of XOS and 600 mg of one of the kiwifruit extract powders.

In still further embodiments the composition consists essentially of XOS and a kiwifruit extract powder selected from the group consisting of a) green kiwifruit extract powder having >7,500 AUs/g actinidin and b) gold kiwifruit extract powder having >5,000 AUs/g actinidin. In some embodiments the composition consists essentially of 10 mg to 20 g of XOS and 10 mg to 20 g of one of the kiwifruit extract powders with the aforementioned properties. In some embodiments the composition consists essentially of 100 mg to 10 g of XOS and 50 mg to 10 g of one of the kiwifruit extract powders with the aforementioned properties. In other embodiments the composition consists essentially of 500 mg to 5 g of XOS and 300 mg to 5 g of one of the kiwifruit extract powders. In other cases the composition consists essentially of 500 mg to 2 g of XOS and 600 mg of one of the kiwifruit extract powders. In still further embodiments the composition consists essentially of 1 g to 2 g of XOS and 600 mg to 2.4 g of one of the kiwifruit extract powders. In one embodiment the composition consists essentially of 1 to 2 g of XOS and 600 mg of one of the kiwifruit extract powders.

In still further embodiments the composition consists essentially of from 10 mg to 20 g of XOS and from 10 mg to 20 g of a kiwifruit extract powder selected from the group consisting of a) green kiwifruit extract powder having >25,000 AUs/g actinidin and b) gold kiwifruit extract powder having >5,000 AUs/g actinidin. In some embodiments the composition consists essentially of 100 mg to 10 g of XOS and 50 mg to 10 g of one of the kiwifruit extract powders with the aforementioned properties. In other embodiments the composition consists essentially of 500 mg to 5 g of XOS and 300 mg to 5 g of one of the kiwifruit extract powders. In other cases the composition consists essentially of 500 mg to 2 g of XOS and 600 mg of one of the kiwifruit extract powders. In still further embodiments the composition consists essentially of 1 g to 2 g of XOS and 600 mg to 2.4 g of one of the kiwifruit extract powders. In one embodiment the composition consists essentially of 1 to 2 g of XOS and 600 mg of one of the kiwifruit extract powders.

In still further embodiments, compositions include from 10 mg to 20 g of XOS and from 10 mg to 20 g of a combination of green kiwifruit extract powder having >25,000 AUs/g actinidin and gold kiwifruit extract powder having >5,000 AUs/g actinidin containing about 6.6 mg GAE total phenolics/600 mg. The composition may include 100 mg to 10 g of XOS and 50 mg to 10 g of the combination of kiwifruit extract powders having the aforementioned properties. Alternatively, the composition may include 500 mg to 5 g of XOS and 300 mg to 5 g of the combination of kiwifruit extract powders. In still other embodiments, the composition may include 500 mg to 2 g of XOS and 600 mg of the combination of kiwifruit extract powders. In yet other embodiments, the composition includes 1 g to 2 g of XOS and 600 mg to 2.4 g of the combination of kiwifruit extract powders. In other embodiments, the composition has 1 g to 2 g of XOS and 600 mg of the combination of kiwifruit extract powders. In still others, the composition has 1 g of XOS and 600 mg of the combination of kiwifruit extract powders.

In still further embodiments, compositions include from 10 mg to 20 g of XOS and from 10 mg to 20 g of a combination of green kiwifruit extract powder containing about 4.8 mg GAE total phenolics/600 mg and >25,000 AUs/g actinidin and gold kiwifruit extract powder containing about 6.6 mg GAE total phenolics/600 mg and >5,000 AUs/g actinidin. The composition may include 100 mg to 10 g of XOS and 50 mg to 10 g of the combination of kiwifruit extract powders having the aforementioned characteristics. Alternatively, the composition may include 500 mg to 5 g of XOS and 300 mg to 5 g of the combination of kiwifruit extract powders. In still other embodiments, the composition may include 500 mg to 2 g of XOS and 600 mg of the combination of kiwifruit extract powders. In yet other embodiments, the composition includes 1 g to 2 g of XOS and 600 mg to 2.4 g of the combination of kiwifruit extract powders. In other embodiments, the composition has 1 g to 2 g of XOS and 600 mg of the combination of kiwifruit extract powders. In still others, the composition has 1 g of XOS and 600 mg of the combination of kiwifruit extract powders.

In still further embodiments the composition consists essentially of from 10 mg to 20 g of XOS and from 10 mg to 20 g of a combination of green kiwifruit extract powder having >25,000 AUs/g actinidin and gold kiwifruit extract powder containing about 6.6 mg GAE total phenolics/600 mg.

In still further embodiments the composition consists essentially of from 10 mg to 20 g of XOS and from 10 mg to 20 g of a combination of green kiwifruit extract powder containing about 4.8 mg GAE total phenolics/600 mg and >25,000 AUs/g actinidin and gold kiwifruit extract powder containing about 6.6 mg GAE total phenolics/600 mg and >5,000 AUs/g actinidin.

BRIEF DESCRIPTION OF THE DRAWINGS

To assist those of ordinary skill in the relevant art in making and using the subject matter hereof, reference is made to the appended drawings, wherein:

FIG. 1 is a graphical depiction of data obtained from in vitro testing of XOS and kiwifruit extract.

It should be noted that the appended drawings illustrate only typical embodiments of this invention and are therefore not to be construed as limiting of its scope, for the invention may admit to other equally effective embodiments.

DETAILED DESCRIPTION OF THE INVENTION

Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Disclosed herein are compositions including green and/or gold kiwifruit extract such as but not limited to Actazin™ and/or Livaux™, respectively, in combination with an XOS prebiotic containing 50-98% xylobiose, xylotriose and/or xylotetraose by weight of the XOS prebiotic, such as PreticX™. The compositions are safe and effective to increase stool frequency in otherwise healthy individuals having ≤3 complete spontaneous bowel movements per week.

In healthy individuals, constipation is characterized by infrequent defecation, yet there remains a diagnostic grey zone between the definition of normal bowel function and functional constipation. Due to the challenges of defining constipation and the inconsistency of results when using a healthy population, complete spontaneous bowel movements (CSBM) has been regarded as a better measurement of bowel habits in healthy individuals. CSBMs are defined as bowel movements that are both spontaneous (i.e., without medication or manual maneuvers) and provide the feeling of complete evacuation (Udani, J. K., & Bloom, D. W. (2013). Effects of Kivia powder on gut health in patients with occasional constipation: a randomized, double-blind, placebo-controlled study. *Nutrition Journal*, 12, 78. https://doi.org/10.1186/1475-2891-12-78). Further, CSBMs may be a valuable parameter to measure for clinical research into the bowel habits of healthy populations as this measure not only provides an indication of stool frequency but also a reflection of the quality of life. Currently, bowel movements are considered an issue only when the frequency is less than 3 times per week. A change of 1 BM per week is already considered as clinically significant.

Nutritional information for Actazin™ green kiwifruit powder is contained in Table 1.

TABLE 1

Actazin™ Green Kiwifruit Powder (Anagenix)
Nutrition Information
Serving size: 600 mg (1 to 4 servings daily)

| | Average Quantity per Serving | Average Quantity per 100 g |
|---|---|---|
| Energy, kJ | 8.6 | 1435 |
| Protein, g | 0.020 | 3.4 |
| Fat, total, g | 0.018 | 3.0 |
| Saturated, g | 0.0039 | 0.75 |
| Unsaturated, g | 0.014 | 2.4 |
| Monounsaturated, g | 0.0032 | 0.53 |
| Polyunsaturated, g | 0.0011 | 1.8 |
| Carbohydrate, g | 0.40 | 67 |
| Sugars, total, g | 0.28 | 46 |
| Glucose, g | 0.13 | 21 |
| Fructose, g | 0.15 | 25 |
| Lactose, g | <0.05 | <0.05 |
| Maltose, g | <0.05 | <0.05 |
| Sucrose, g | <0.05 | <0.05 |
| Dietary fibre, g | 0.093 | 16 |
| Sodium, mg | 0.080 | 13 |
| Total phenolics, mg GAE | 4.8 | 800 |
| Actinidin AUs | >15,000 AUs (based on >>25,000 AUs/g) | >2,500,000 AUs |

Nutritional information for Livaux™ gold kiwifruit powder is contained in Table 2.

TABLE 2

Livaux™ Gold Kiwifruit Powder (Anagenix)
Nutrition Information
Serving size: 600 mg (1 to 4 servings daily)

| | Average Quantity per Serving | Average Quantity per 100 g |
|---|---|---|
| Energy, kJ | 8.5 | 1420 |
| Protein, g | 0.02 | 3.9 |
| Fat, total, g | 0.01 | 1.8 |
| Saturated, g | 0.002 | 0.34 |
| Unsaturated, g | 0.01 | 1.4 |
| Monounsaturated, g | <0.10 | <0.10 |
| Polyunsaturated, g | 0.01 | 1.4 |
| Carbohydrate, g | 0.42 | 71 |
| Sugars, total, g | 0.35 | 58 |
| Glucose, g | 0.16 | 27 |
| Fructose, g | 0.19 | 31 |
| Lactose, g | <0.05 | <0.05 |
| Maltose, g | <0.05 | <0.05 |
| Sucrose, g | <0.05 | <0.05 |
| Dietary fibre, g | 0.06 | 9.8 |
| Insoluble fibre, g | 0.05 | 8.8 |
| Soluble fibre, g | 0.01 | 1.0 |
| Sodium, mg | 0.11 | 18 |
| Total phenolics, mg GAE | 6.6 | 1100 |
| Actinidin AUs | 3,000 (based on >5,000 AUs/g) | >500,000 |

The abbreviation GAE refers to gallic acid equivalents. The abbreviation AU refers to activity units and AUs/g refers to activity units per gram. The substrate used to monitor activity levels of actinidin in Actazin and Livaux is N-α-CBZ-lysine p-nitrophenol with digestion at 25° C. The method is set forth in Boland M J, Hardman M J, Kinetic studies on the thiol protease from *Actinidia chinensis*. FEBS Lett 1972; 27:282-4, incorporated by reference herein in its entirety.

Table 3 includes specifications for various forms of PreticX™ XOS compositions.

TABLE 3

Specifications of PreticX™ XOS preparations

| Item | XOS 95P Powder | XOS 70P Powder | XOS 35P Powder | XOS 20P Powder | Analytical method |
|---|---|---|---|---|---|
| Dry substance, % | ≥95 | ≥95 | ≥95 | ≥95 | |
| Moisture, % | ≤6.0 | ≤6.0 | ≤6.0 | ≤6.0 | AOAC 934.01 |
| Ash, % | ≤0.3 | ≤0.3 | ≤0.3 | ≤0.3 | AOAC 900.02 |
| XOS content, % dry wt. basis | ≥93% | ≥68% | ≥35% | ≥20% | MHLW*, 2005 |
| XOS content, % as-is basis | ≥88.4% | ≥64.6% | ≥33.25% | ≥19.0% | MHLW*, 2005 |
| Arsenic, ppm by wt. | ≤0.3 | ≤0.3 | ≤0.3 | ≤0.3 | |
| Lead, ppm by wt. | ≤0.5 | ≤0.5 | ≤0.5 | ≤0.5 | |

*MHLW (Ministry of Health, Labor and Welfare of Japan), 2005 = modified AOAC method 2001.03 (measured xylose oligomers instead of glucose oligomers)

Table 4 includes intended use levels for various forms of PreticX™ XOS compositions. The abbreviation NMT means "not more than".

TABLE 4

Intended use levels (g per serving) of various PreticX ™ XOS ingredients.

| Item | XOS 95 Powder | XOS 70 Powder | XOS 35 Powder | XOS 20 Powder |
|---|---|---|---|---|
| Dry substance, % | ≥95 | ≥95 | ≥95 | ≥95 |
| Moisture, % | ≤6.0 | ≤6.0 | ≤6.0 | ≤6.0 |
| XOS content, % dry wt. basis | ≥93% | ≥68% | ≥35% | ≥20% |
| XOS content, As-is basis | ≥88.4% | ≥64.6% | ≥33.25% | ≥19.0% |
| The amount (g) to deliver 2.0 g XOS per serving | NMT 2.15 | NMT 2.94 | NMT 5.7 | NMT 10.0 |
| The amount (g) to deliver 1.0 g XOS per serving | NMT 1.06 | NMT 1.47 | NMT 2.86 | NMT 5.0 |

Compositions disclosed herein may include the active materials XOS containing 50-98% xylobiose, xylotriose and/or xylotetraose by weight of the XOS prebiotic and kiwifruit extract powders in various combinations. For example, in one embodiment a composition is disclosed having from 10 mg to 20 g of XOS and from 10 mg to 20 g of Actazin™ or Livaux™. In another, a composition has from 10 mg to 20 g of XOS and from 10 mg to 20 g of a combination of Actazin™ and Livaux™. In still another, the composition has from 100 mg to 10 g of XOS and from 50 mg to 10 g of a combination of Actazin™ and Livaux™. In yet a further embodiment a composition is disclosed having from 100 mg to 10 g of XOS and from 50 mg to 10 g of Actazin™ or Livaux™. In another example the composition has from 500 mg to 5 g of XOS and from 300 mg to 5 g of a combination of Actazin™ and Livaux™. In another embodiment a composition includes from 500 mg to 5 g of XOS and from 300 mg to 5 g of Actazin™ or Livaux™. In yet another, a composition includes from 1 g to 2 g of XOS and from 600 mg to 2.4 g of Actazin™ or Livaux™.

In other embodiments, a composition may include from 1 g to 2 g of XOS and from 600 mg to 2.4 g of a combination of Actazin™ and Livaux™. In one embodiment the composition includes 1-2 g of PreticX™ prebiotic (95%) and 600 mg of Actazin™ or Livaux™. In another, the composition includes 500 mg-2 g of PreticX™ prebiotic (95%) and 600 mg of Actazin™ or Livaux™. Alternatively the composition may include 1-2 g of PreticX™ prebiotic (95%) and 600 mg of a combination of Actazin™ and Livaux™. The composition may include 500 mg-2 g of PreticX™ prebiotic (95%) and 600 mg of a combination of Actazin™ and Livaux™.

In other embodiments the composition includes 1-4 g of PreticX™ prebiotic (70%) and 600 mg of Actazin™ or Livaux™. In another, the composition includes 500 mg-4 g of PreticX™ prebiotic (70%) and 600 mg of Actazin™ or Livaux™. Alternatively the composition may include 1-4 g of PreticX™ prebiotic (70%) and 600 mg of a combination of Actazin™ and Livaux™. The composition may include 500 mg-4 g of PreticX™ prebiotic (70%) and 600 mg of a combination of Actazin™ and Livaux™.

In another embodiment the composition includes PreticX™ having 1 g of XOS and 600 mg of a combination of Actazin™ and Livaux™. The composition may include PreticX™ having 1 g of XOS and 600 mg of Actazin™ or Livaux™.

All XOS disclosed herein, including all forms of PreticX™, contain 50-98% by weight xylobiose, xylotriose and/or xylotetraose of the total XOS profile, as measured by HPLC. This is the case for all PreticX™ XOS prebiotics regardless of the strength. In other embodiments xylobiose, xylotriose and/or xylotetraose account for 60-95% by weight of the total xylooligosaccharide profile of the XOS prebiotic. In still other embodiments xylobiose, xylotriose and/or xylotetraose account for at least 70% by weight of the total xylooligosaccharide profile of the XOS prebiotic. In yet other embodiments xylobiose, xylotriose and/or xylotetraose account for at least 80% by weight of the total xylooligosaccharide profile of the XOS prebiotic. In yet other embodiments xylobiose, xylotriose and/or xylotetraose account for at least 90% by weight of the total xylooligosaccharide profile of the XOS prebiotic.

Furthermore, in some embodiments xylobiose accounts for 25-70% by weight of the total xylooligosaccharide profile of the XOS prebiotic. In other embodiments xylobiose accounts for 30-60% by weight of the total xylooligosaccharide profile of the XOS prebiotic. In still other embodiments xylobiose accounts for at least 25% by weight of the total xylooligosaccharide profile of the XOS prebiotic. In still other embodiments xylobiose accounts for at least 30% by weight of the total xylooligosaccharide profile of the XOS prebiotic. In still other embodiments xylobiose accounts for at least 35% by weight of the total xylooligosaccharide profile of the XOS prebiotic. In still other embodiments xylobiose accounts for at least 40% by weight of the total xylooligosaccharide profile of the XOS prebiotic. In still other embodiments xylobiose accounts for at least 50% by weight of the total xylooligosaccharide profile of the XOS prebiotic.

In other embodiments xylotriose accounts for 20-50% by weight of the total xylooligosaccharide profile of the XOS prebiotic. In other embodiments xylotriose accounts for 25-35% by weight of the total xylooligosaccharide profile of the XOS prebiotic. In still other embodiments xylotriose accounts for at least 25% by weight of the total xylooligosaccharide profile of the XOS prebiotic. In still other embodiments xylotriose accounts for at least 30% by weight of the total xylooligosaccharide profile of the XOS prebiotic. In still other embodiments xylotriose accounts for at least 35% by weight of the total xylooligosaccharide profile of the XOS prebiotic.

In some embodiments xylotetraose may account for 5-25% by weight of the total xylooligosaccharide profile of the XOS prebiotic. In some embodiments xylotetraose accounts for 6-20% by weight of the total xylooligosaccharide profile of the XOS prebiotic. In other embodiments xylotetraose may account for at least 10% by weight of the total xylooligosaccharide profile of the XOS prebiotic. In other embodiments xylotetraose may account for at least 15% by weight of the total xylooligosaccharide profile of the XOS prebiotic. In other embodiments xylotetraose may account for at least 17% by weight of the total xylooligosaccharide profile of the XOS prebiotic.

Xylooligosaccharides such as those contained in PreticX™ may be obtained by breaking down xylan-containing raw materials, such as corncob, sugarcane, etc., to powder and mixing the powder with water; subjecting the mixture to heat and acid treatment under high pressure to break down the hemicelluloses present in the raw material; and subsequently, adding enzymes, such as xylanase, to the mixture to hydrolyze beta-1,4-xylosidic bonds in the beta-(1,4)-linked D-xylosyl backbone of xylan into XOS. The liquid is then separated from the hydrolysis products using a liquid-slag separator. A decoloring step may be employed to remove the pigment and other impurities. The material may then be subjected to an ion exchange process and filtration, and subsequently, concentrated. The saccharide content may be adjusted by addition of one or more excipients such as but not limited to maltodextrin. The material may then be spray dried.

Using special care in the addition of enzymes and enzymatic conditions may enrich the short chain $n=_{2-4}$ XOS, wherein n denotes the number of xylo units. For example, xylotetraose has 4 xylose units, xylotriose has 3 xylo units and xylobiose has 2 xylo units. It is known from literature that shorter chain of XOS, especially bi-, tri- and tetra-XOS, are more effective for prebiotic benefits, thus the short-chain enriched XOS, as found in PreticX™ XOS, is much more effective and can be used at a much lower dosage. Examples of XOS profiles for PreticX are shown in Table 5.

TABLE 5

| Sample # | 1 | 2 | 3 | 4 | 5 | 6 |
|---|---|---|---|---|---|---|
| X(2-4) | 86.62 | 79.56 | 78.12 | 94.28 | 77.20 | 81.30 |
| X2 | 37.08 | 34.00 | 31.55 | 53.84 | 30.17 | 35.93 |
| X3 | 31.52 | 29.13 | 29.52 | 34.42 | 28.99 | 32.84 |
| X4 | 17.52 | 16.51 | 17.05 | 6.02 | 18.04 | 12.53 |

Suitable routes of administration may include, without limitation, oral, rectal, transmucosal or intestinal administration. In certain embodiments, the preferred route is oral.

Compositions of the present invention may be manufactured by processes well known in the art, e.g., by means of conventional mixing, dissolving, granulating, dragee-making, levigating, emulsifying, encapsulating, entrapping or lyophilizing processes. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; and H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

The compositions disclosed herein may consist of only XOS and either or both of green and gold kiwifruit extract. Compositions in accordance with the present invention can be included in foods and beverages, food additives, animal feeds and feed additives as well as compositions including pharmaceutically acceptable carriers. Compositions may be formulated in any conventional manner using one or more physiologically acceptable carriers comprising excipients and auxiliaries which facilitate processing of the active compositions into preparations which can be used nutraceutically or pharmaceutically. Proper formulation is dependent upon the route of administration chosen.

For oral administration, the compositions can be formulated by combining the components with nutraceutically or pharmaceutically acceptable carriers well known in the art. Such carriers enable the compositions of the invention to be formulated as powders, tablets, pills, lozenges, dragees, capsules, liquids, gels, syrups, slurries, suspensions and the like, for oral ingestion by an individual. Compositions for oral use can be made using a solid excipient, optionally grinding the resulting mixture, and processing the mixture of granules, after adding other suitable auxiliaries if desired, to obtain powders to be used as an additive to food or beverages, or obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of doses.

Compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, a binder such as starch, and/or a lubricant such as talc or magnesium stearate and, optionally, stabilizers. In soft capsules, the compositions may be dissolved or suspended in suitable liquids, such as fatty oils, liquid paraffin, or liquid polyethylene glycols. Stabilizers may be added in these formulations, also. Compositions which may also be used include hard gelatin capsules. The capsules or pills may be packaged into brown glass or plastic bottles to protect the compositions from light. The containers containing the composition capsule formulation are preferably stored at controlled room temperature (15-30° C.).

The compositions may also be formulated in rectal compositions such as suppositories or retention enemas, using, e.g., conventional suppository bases such as cocoa butter or other glycerides.

Additionally, the compositions may be delivered using a sustained-release system, such as semipermeable matrices of solid hydrophobic polymers containing the composition. Various sustained-release materials have been established and are well known by those skilled in the art. Sustained-release capsules may, depending on their chemical nature, release the compositions for a few weeks up to over 100 days. The compositions herein also may include suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Compositions suitable for use in the present invention include compositions wherein the active ingredients are contained in an amount sufficient to achieve the intended purpose, e.g., the increase in stool frequency, change in stool form, change of the microbiome, etc. More specifically, a therapeutically effective amount means an amount of composition effective to alleviate or ameliorate symptoms, such as constipation, of disease. Determination of a therapeutically effective amount is well within the capability of those skilled in the art, especially in light of the detailed disclosure provided herein.

The dosage may vary depending upon the dosage form employed and the route of administration utilized.

Prophetic Examples of Formulations

A. TABLETS

| Component | Amount per tablet (mg) |
| --- | --- |
| XOS (PreticX ™ XOS 95) | 500 |
| Green Kiwifruit extract powder (Actazin ™) | 300 |
| lactose | 40 |
| corn starch | 40 |
| polyvinylpyrrolidone | 15 |
| magnesium stearate | 5 |
| TOTAL | 900 |

The XOS and kiwifruit extract powder, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
| --- | --- |
| XOS (PreticX ™ XOS 95) | 500 |
| Green Kiwifruit extract powder (Actazin ™) | 300 |
| lactose | 20 |
| corn starch | 20 |
| polyvinylpyrrolidone | 15 |
| magnesium stearate | 2 |
| microcrystalline cellulose | 23 |
| sodium-carboxymethyl starch | 20 |
| TOTAL | 900 |

The XOS and kiwifruit extract powder, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
| --- | --- |
| XOS (PreticX ™ XOS 95) | 500 |
| Gold Kiwifruit extract powder (Livaux ™) | 300 |
| Lactose | 10 |
| corn starch | 11.5 |
| polyvinylpyrrolidone | 3 |
| magnesium stearate | 0.5 |
| TOTAL | 825 |

The XOS and kiwifruit extract powder, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
| --- | --- |
| XOS (PreticX ™ XOS 95) | 500 |
| Gold Kiwifruit extract powder (Livaux ™) | 300 |
| Green Kiwifruit extract powder (Actazin ™) | 300 |
| TOTAL | 1100 |

The XOS and kiwifruit extract powders are mixed thoroughly to obtain uniformity of content. The finished mixture is packed into suitably sized hard gelatin capsules.

The dosage for an adult may be from about 600-2,400 mg/day of kiwifruit extract powder, which may be green or gold kiwifruit extract powder as described herein, and 1-2 g XOS containing 50-98% xylobiose, xylotriose and/or xylotetraose by weight of the XOS prebiotic, PreticX™ XOS 95, PreticX™ XOS 70, PreticX™ XOS 35 or PreticX™ XOS 20. For example, and not by way of limitation, one capsule from formulation example A, B, C or D may be administered one to four times/day.

Compositions disclosed herein may be in the form of powder or granulate having uniformity of content. Such forms may be packaged in containers from which dosages may be dispensed, such as by spooning the powder into a liquid or food. These forms may be packaged in single dose packets, envelopes or the like. In the following embodiments the term "powder" is used broadly to refer to powder, granulate or other well-known dry forms, in bulk or otherwise.

In the following embodiments XOS refers to either XOS containing 50-98% xylobiose, xylotriose and/or xylotetraose by weight of the XOS prebiotic, PreticX™ XOS 95, PreticX™ XOS 70, PreticX™ XOS 35 or PreticX™ XOS 20.

In one embodiment the powder contains from 1-99% w/w XOS and from 1-99% w/w green kiwifruit extract powder having >7,500 AUs/g, and preferably >25,000 AUs/g, actinidin, and optionally about 4.8 mg GAE total phenolics/600 mg. In another embodiment the powder contains from 1-99% XOS w/w and from 1-99% w/w gold kiwifruit extract powder having >5,000 AUs/g actinidin and optionally about 6.6 mg GAE total phenolics/600 mg. In still further embodiments the powder contains from 1-99% XOS w/w and 1-99% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 5-95% w/w XOS and from 5-95% w/w green kiwifruit extract powder having >7,500 AUs/g, and preferably >25,000 AUs/g, actinidin, and optionally about 4.8 mg GAE total phenolics/600 mg. In another embodiment the powder contains from 5-95% XOS w/w and from 5-95% w/w gold kiwifruit extract powder having >5,000 AUs/g actinidin and optionally about 6.6 mg GAE total phenolics/600 mg actinidin. In still further embodiments the powder contains from 5-95% XOS w/w and 5-95% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 10-90% w/w XOS and from 10-90% w/w green kiwifruit extract powder having >7,500 AUs/g, and preferably >25,000 AUs/g, actinidin, and optionally about 4.8 mg GAE total phenolics/600 mg. In another embodiment the powder contains from 10-90% XOS w/w and from 10-90% w/gold kiwifruit extract powder having >5,000 AUs/g actinidin and optionally about 6.6 mg GAE total phenolics/600 mg. In still further embodiments the powder contains from 10-90% XOS w/w and 10-90% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 15-85% w/w XOS and from 15-85% w/w green kiwifruit extract powder having >7,500 AUs/g, and preferably >25,000 AUs/g, actinidin, and optionally about 4.8 mg GAE total phenolics/600 mg. In another embodiment the powder contains from 15-85% XOS w/w and from 15-85% w/w gold kiwifruit extract powder having >5,000 AUs/g actinidin and optionally about 6.6 mg GAE total phenolics/600 mg. In still further embodiments the powder contains from 15-85% XOS w/w and 15-85% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 20-80% w/w XOS and from 20-80% w/w green kiwifruit extract powder having >7,500 AUs/g, and preferably >25,000 AUs/g, actinidin, and optionally about 4.8 mg GAE total phenolics/600 mg. In another embodiment the powder contains from 20-80% XOS w/w and from 20-80% w/w gold kiwifruit extract powder having >5,000 AUs/g actinidin and optionally about 6.6 mg GAE total phenolics/600 mg. In still further embodiments the powder contains from 20-80% XOS w/w and 20-80% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 25-75% w/w XOS and from 25-75% w/w green kiwifruit extract powder having >7,500 AUs/g, and preferably >25,000 AUs/g, actinidin, and optionally about 4.8 mg GAE total phenolics/600 mg. In another embodiment the powder contains from 25-75% XOS w/w and from 25-75% w/w gold kiwifruit extract powder having >5,000 AUs/g actinidin and optionally about 6.6 mg GAE total phenolics/600 mg. In still further embodiments the powder contains from 25-75% XOS w/w and 25-75% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 30-70% w/w XOS and from 30-70% w/w green kiwifruit extract powder having >7,500 AUs/g, and preferably >25,000 AUs/g, actinidin, and optionally about 4.8 mg GAE total phenolics/600 mg. In another embodiment the powder contains from 30-70% XOS w/w and from 30-70% w/w gold kiwifruit extract powder having >5,000 AUs/g actinidin and optionally about 6.6 mg GAE total phenolics/600 mg. In still further embodiments the powder contains from 30-70% XOS w/w and 30-70% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 35-65% w/w XOS and from 35-65% w/w green kiwifruit extract powder having >7,500 AUs/g, and preferably >25,000 AUs/g, actinidin, and optionally about 4.8 mg GAE total phenolics/600 mg. In another embodiment the powder contains from 35-65% XOS w/w and from 35-65% w/w gold kiwifruit extract powder having >5,000 AUs/g actinidin and optionally about 6.6 mg GAE total phenolics/600 mg. In still further embodiments the powder contains from 35-65% XOS w/w and 35-65% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 40-60% w/w XOS and from 40-60% w/w green kiwifruit extract powder having >7,500 AUs/g, and preferably >25,000 AUs/g, actinidin, and optionally about 4.8 mg GAE total phenolics/600 mg. In another embodiment the powder contains from 40-60% XOS w/w and from 40-60% w/w gold kiwifruit extract powder having >5,000 AUs/g actinidin and optionally about 6.6 mg GAE total phenolics/600 mg. In still further embodiments the powder contains from 40-60% XOS w/w and 40-60% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains from 45-55% w/w XOS and from 45-55% w/w green kiwifruit extract powder having >7,500 AUs/g, and preferably >25,000 AUs/g, actinidin, and optionally about 4.8 mg GAE total phenolics/600 mg. In another embodiment the powder contains from 45-55% XOS w/w and from 45-55% w/w gold kiwifruit extract powder having >5,000 AUs/g actinidin and optionally about 6.6 mg GAE total phenolics/600 mg. In still further embodiments the powder contains from 45-55% XOS w/w and 45-55% w/w of a mixture of green and gold kiwifruit extract powder as characterized above. In this embodiment, the ratio of green kiwifruit extract powder to gold kiwifruit extract powder may, by weight, be from 1:100 to 100:1.

In still further embodiments, the powder contains 50% w/w XOS and 50% w/w green kiwifruit extract powder having >7,500 AUs/g, and preferably >25,000 AUs/g, actinidin, and optionally about 4.8 mg GAE total phenolics/600 mg. In another embodiment the powder contains 50% XOS w/w and 50% w/w gold kiwifruit extract powder having >5,000 AUs/g actinidin and optionally about 6.6 mg GAE total phenolics/600 mg. In still further embodiments the powder contains 50% XOS w/w and 50% w/w of a mixture of green and gold kiwifruit extract powder as characterized above. In this embodiment, the ratio of green kiwifruit extract powder to gold kiwifruit extract powder may, by weight, be from 1:100 to 100:1.

In yet further embodiments, the powder contains 62.5% w/w XOS and 37.5% w/w green kiwifruit extract powder having >7,500 AUs/g, and preferably >25,000 AUs/g, actinidin, and optionally about 4.8 mg GAE total phenolics/600 mg. In another embodiment the powder contains 62.5% XOS w/w and 37.5% w/w gold kiwifruit extract powder having >5,000 AUs/g actinidin and optionally about 6.6 mg GAE total phenolics/600 mg. In still further embodiments the powder contains 62.5% XOS w/w and 37.5% w/w of a mixture of green and gold kiwifruit extract powder as characterized above. In this embodiment, the ratio of green kiwifruit extract powder to gold kiwifruit extract powder may, by weight, be from 1:100 to 100:1.

In yet still a further embodiment, the powder contains 76.9% w/w XOS and 23.1% w/w green kiwifruit extract powder having >7,500 AUs/g, and preferably >25,000 AUs/g, actinidin, and optionally about 4.8 mg GAE total phenolics/600 mg. In another embodiment the powder contains 76.9% XOS w/w and 23.1% w/w gold kiwifruit extract powder having >5,000 AUs/g actinidin and optionally about 6.6 mg GAE total phenolics/600 mg. In still further embodiments the powder contains 76.9% XOS w/w and 23.1% w/w of a mixture of green and gold kiwifruit extract powder as characterized above. In this embodiment, the ratio of green kiwifruit extract powder to gold kiwifruit extract powder may, by weight, be from 1:100 to 100:1.

In other embodiments the powder contains 29.4% w/w XOS and 70.6% w/w green kiwifruit extract powder having >7,500 AUs/g, and preferably >25,000 AUs/g, actinidin, and optionally about 4.8 mg GAE total phenolics/600 mg. In another embodiment the powder contains 29.4% XOS w/w and 70.6% w/w gold kiwifruit extract powder having >5,000 AUs/g actinidin and optionally about 6.6 mg GAE total phenolics/600 mg. In still further embodiments the powder contains 29.4% XOS w/w and 70.6% w/w of a mixture of green and gold kiwifruit extract powder as characterized above. In this embodiment, the ratio of green kiwifruit extract powder to gold kiwifruit extract powder may, by weight, be from 1:100 to 100:1.

In further embodiments the powder contains 45.5% w/w XOS and 54.5% w/w green kiwifruit extract powder having >7,500 AUs/g, and preferably >25,000 AUs/g, actinidin, and optionally about 4.8 mg GAE total phenolics/600 mg. In another embodiment the powder contains 45.5% XOS w/w and 54.5% w/w gold kiwifruit extract powder having >5,000 AUs/g actinidin and optionally about 6.6 mg GAE total phenolics/600 mg. In still further embodiments the powder contains 45.5% XOS w/w and 54.5% w/w of a mixture of green and gold kiwifruit extract powder as characterized above. In this embodiment, the ratio of green kiwifruit extract powder to gold kiwifruit extract powder may, by weight, be from 1:100 to 100:1.

For any composition disclosed herein, the therapeutically effective amount or dose for a sample of the population can be estimated initially from a multi-center, randomized double-blind placebo-controlled parallel study to evaluate the efficacy of the composition on complete spontaneous bowel movements (CSBM) in participants who normally have ≤3 complete spontaneous bowel movements per week but are otherwise healthy. For example, a study may include 240 participants randomized into 6 groups in a double-blind manner at a ratio of 1:1:1:1:1:1 as set forth in Table 6.

TABLE 6

| Study Arm | Number of Participants | Capsules Taken Daily |
| --- | --- | --- |
| Group 1: Placebo | N = 40 | 4x placebo |
| Group 2: Actazin-High Dose (2400 mg) | N = 40 | 4x Actazin |
| Group 3: Actazin-Low Dose (600 mg) | N = 40 | 1x Actazin + 3x placebo |
| Group 4: Formula (Actazin 600 mg + PreticX (70%) (1400 mg) | N = 40 | 1x Actazin + 3x PreticX |

TABLE 6-continued

| Study Arm | Number of Participants | Capsules Taken Daily |
| --- | --- | --- |
| Group 5: Livaux-H (2400 mg) | N = 40 | 4x Livaux |
| Group 6: Livaux-L (600 mg) | N = 40 | 1x Livaux + 3x placebo |
| Total | N = 240 | 4 capsules/day/participant |

A CSBM is defined as bowel movements that are both complete and spontaneous. CSBM is an accepted and easily defined primary measure of stool frequency in clinical trials assessing bowel habits (U. S. Department of Health and Human Services, Food and Drug Administration, & Centre for Drug Evaluation and Research (CDER), 2012). A primary objective could be defined as an improvement of 1 CSBM/week in a population of participants who normally have ≤3 CS BM/week as assessed by the daily bowel habits diary (BHD) from baseline to completion of the study.

Secondary objectives could be defined as:
1. The change in spontaneous bowel movements per week as assessed by the daily bowel habits diary (BHD) from baseline to completion between Actazin-H, Actazin-L, Livaux-H, Livaux-L, Formula, and placebo;
2. The change in stool form as assessed by the Bristol Stool Scale (BSS) from baseline to completion between Actazin-H, Actazin-L, Livaux-H, Livaux-L, Formula, and placebo;
3. The change in interval between bowel movements in hours from baseline to completion between Actazin-H, Actazin-L, Livaux-H, Livaux-L, Formula, and placebo;
4. The time of occurrence of bowel movements in Actazin-H, Actazin-L, Livaux-H, Livaux-L, Formula, and placebo from baseline to completion;
5. The change in blood calcium levels as assessed by fasted blood sample analysis from baseline to completion between Actazin-H, Actazin-L, Livaux-H, Livaux-L, Formula, and placebo;
6. The change in fasting glucose levels as assessed by fasted blood sample analysis from baseline to completion between Actazin-H, Actazin-L, Livaux-H, Livaux-L, Formula, and placebo;
7. The change in a patient assessment of constipation symptoms questionnaire from baseline to completion between Actazin-H, Actazin-L, Livaux-H, Livaux-L, Formula, and placebo;
8. The change in a patient assessment of constipation quality of life questionnaire from baseline to completion between Actazin-H, Actazin-L, Livaux-H, Livaux-L, Formula, and placebo;
9. The change in gut microbiome as assessed by fecal sample analysis from baseline to completion between Actazin-H, Actazin-L, Livaux-H, Livaux-L, Formula, and placebo;
10. Percentage (%) of early and late responders to Actazin-H, Actazin-L, Livaux-H, Livaux-L, Formula, and placebo product as assessed by a bowel habits diary; and
11. The difference in the Bowel Regularity Index at completion between Actazin-H, Actazin-L, Livaux-H, Livaux-L, Formula, and placebo In order to evaluate primary, secondary, and safety outcomes, study assessments can be conducted at baseline and all study visits. The study would be subject to certain criteria. For example, the study could include 240 healthy male and female participants with ≤3 bowel movements per week who meet the inclusion criteria and not meet any of the exclusion criteria. These criteria could include criteria well-known to those skilled in the art. For example, and not by way of limitation, criteria could include age (e.g., 18-60 years), body mass index (BMI) (e.g., 19-30 kg/m²), blood glucose level (e.g., fasting blood glucose less than 5.6 mmol/L). Exclusion criteria could include, for example, the presence of gastrointestinal alarm symptoms such as but not limited to blood in stools, frequent diarrhea, unremitting abdominal pain, etc.); dietary extremes, such as but not limited to liquid, vegan, or high-fiber diets; gastroparesis or lactose intolerance; surgery for weight loss (lap band or gastric bypass); clinically significant renal, hepatic, endocrine, cardiac, pulmonary, pancreatic, neurologic, hematologic, or biliary disorders as disclosed or detected through a comprehensive metabolic panel taken at initial screening; pregnancy; allergy or sensitivity to XOS or kiwifruit.

Non-excluded participants who taking any prescribed medications would agree to maintain their current method and dosing regimen during the course of the study unless recommended by their physician. Certain prescribed medications could be grounds for exclusion if cessation were not possible. Consumption of certain over-the-counter medications, supplements, and foods/drinks such as high-fiber supplements (e.g. *psyllium* and wheat bran, Metamucil® (Procter & Gamble), Benefiber® (GlaxoSmithKline), Phloe® (Douglas Pharmaceuticals)), very high-fiber diet greater than 25 g/day for females and 30 g/day for males, and fresh kiwifruit could be grounds for exclusion if cessation or a wash-out period were not possible.

Participants could be required to record food intake and collect stool for analysis. Participants could be asked to complete a questionnaire including questions about numbers of bowel movements; incomplete and assisted bowel movements; assessment of stools on the Bristol stool scale; and about bloating, flatulence, laxatives, and abdominal pain. The Bristol stool score, which is well known to those skilled in the art, requires assigning a score on a scale of 1-7 the appearance of the stool.

Experiments

XOS, Actazin™ kiwifruit extract and Livaux™ kiwifruit extract each individually contribute to gut health. XOS promotes the growth of good bacteria, especially *Bifidobacterium*, while Actazin™ and Livaux™ modulate the microbiota via kiwi-specific prebiotics. In vitro experimentation surprisingly showed a synergistic effect when PreticX™ XOS and Actazin™ were combined.

PreticX™ XOS (95%), Actazin™, and PreticX™ XOS (95%)+Actazin™ were tested for their ability to grow *Bifidobacterium animalis* ss *lactis* strain under anaerobic conditions.

1 g/100 ml of PreticX™ XOS (95%), 1 g/100 ml of Actazin™, and 1 g PreticX™ XOS (95%)+1 g of Actazin™/100 ml solutions were prepared using sterile water. 20 µl of each of the above solutions and 180 µl of the *Bifidobacterium animalis* ss *lactis* cell suspension (1% v/v) were added to micro-plate wells of the automatic Bioscreen® C system. The plates were incubated at 37° C. for 24 hours under anaerobic condition and the optical density was measured at 600 nm once every 30 minutes.

The bacterial growth was determined as the area under the growth curve (OD600×min) and the growth in the blank control medium (MRS without added carbohydrates) was subtracted from results. Data are presented for an average of three replicates. With reference to FIG. 1, the average area under the growth curve is 236 for PreticX™ XOS (95%), 84 for Actazin™, and 426 for PreticX™ XOS (95%)+Actazin™, indicating a synergistic effect of for PreticX™ XOS (95%)+Actazin™ in promoting the growth of *Bifidobacterium animalis* ss *lactis*.

Although the compositions of the present disclosure have been described with reference to exemplary embodiments thereof, the present disclosure is not limited thereby. Indeed, the exemplary embodiments are implementations of the disclosed compositions are provided for illustrative and non-limitative purposes. Changes, modifications, enhancements and/or refinements to the disclosed compositions may be made without departing from the spirit or scope of the present disclosure. Accordingly, such changes, modifications, enhancements and/or refinements are encompassed within the scope of the present invention. All references cited herein are incorporated by reference in their entirety.

What is claimed is:

1. A composition comprising concentrated xylooligosaccharides (XOS) obtained by subjecting a xylan-containing material to heat and acid treatment, adding an enzyme, and filtering, wherein xylobiose, xylotriose and/or xylotetraose account for 50-98% by weight of the concentrated XOS and the composition further comprises a kiwifruit extract powder selected from the group consisting of a) green kiwifruit extract powder comprising >7,500 AUs/g actinidin and b) gold kiwifruit extract powder comprising >5,000 AUs/g actinidin.

2. The composition of claim 1 wherein the kiwifruit extract powder is green kiwifruit extract powder comprising >25,000 AUs/g actinidin.

3. The composition of claim 1 wherein the kiwifruit extract powder is green kiwifruit extract powder comprising about 4.8 mg gallic acid equivalents (GAE) total phenolics/600 mg.

4. The composition of claim 1 wherein the kiwifruit extract powder is gold kiwifruit extract powder comprising about 6.6 mg gallic acid equivalents (GAE) total phenolics/600 mg.

5. The composition of claim 1 comprising 100 mg to 10 g of the concentrated XOS and 50 mg to 10 g of the kiwifruit extract powder.

6. The composition of claim 1 comprising 500 mg to 5 g of the concentrated XOS and 300 mg to 5 g of the kiwifruit extract powder.

7. The composition of claim 6 comprising 500 mg to 2 g of the concentrated XOS and 600 mg of the kiwifruit extract powder.

8. The composition of claim 1 comprising 1 g to 2 g of the concentrated XOS and 600 mg to 2.4 g of the kiwifruit extract powder.

9. The composition of claim 8 comprising 600 mg of the kiwifruit extract powder.

10. The composition of claim 1 wherein xylobiose, xylotriose and/or xylotetraose account for 50-70% by weight of the concentrated XOS.

11. The composition of claim 1 wherein xylobiose accounts for 25-70% by weight of the concentrated XOS.

12. The composition of claim 1 wherein xylotetraose accounts for 5-25% by weight of the concentrated XOS.

13. The composition of claim 1 in the form of a powder consisting essentially of the concentrated XOS and one of the kiwifruit extract powders.

14. A composition comprising concentrated XOS obtained by subjecting a xylan-containing material to heat and acid treatment, adding an enzyme, and filtering, wherein xylobiose, xylotriose and/or xylotetraose account for 50-98% by weight of the XOS and the composition further comprises a combination of green kiwifruit extract powder comprising >7,500 AUs/g actinidin and gold kiwifruit extract powder comprising >5,000 AUs/g actinidin.

15. The composition of claim 14 wherein the green kiwifruit extract powder comprises >25,000 AUs/g actinidin.

16. The composition of claim 14 wherein the green kiwifruit extract powder comprises about 4.8 mg GAE total phenolics/600 mg.

17. The composition of claim 14 wherein the gold kiwifruit extract powder comprises about 6.6 mg GAE total phenolics/600 mg.

18. The composition of claim 14 comprising 100 mg to 10 g of the concentrated XOS and 50 mg to 10 g of the combination of kiwifruit extract powders.

19. The composition of claim 14 comprising 500 mg to 5 g of the concentrated XOS and 300 mg to 5 g of the combination of kiwifruit extract powders.

20. The composition of claim 14 comprising 500 mg to 2 g of the concentrated XOS and 600 mg of the combination of kiwifruit extract powders.

21. The composition of claim 14 comprising 1 g to 2 g of the concentrated XOS and 600 mg to 2.4 g of the combination of kiwifruit extract powders.

22. The composition of claim 21 comprising 600 mg of the combination of kiwifruit extract powders and 1 g of the concentrated XOS.

\* \* \* \* \*